United States Patent [19]

Hayashi et al.

[11] Patent Number: 4,959,097
[45] Date of Patent: Sep. 25, 1990

[54] 23-PHENYLSTEROIDS

[75] Inventors: Sei-ichi Hayashi; Tadashi Hohjoh, both of Saitama; Atsuhiko Shida, Ibaraki; Nobuo Ikekawa, Tokyo, all of Japan

[73] Assignees: Nippon Kayaku Kabushiki Kaisha; Tama Biochemical Co., Ltd., both of Tokyo, Japan

[21] Appl. No.: 416,926

[22] Filed: Oct. 4, 1989

Related U.S. Application Data

[62] Division of Ser. No. 163,526, Mar. 3, 1988, Pat. No. 4,886,544.

[30] Foreign Application Priority Data

Mar. 17, 1987 [JP] Japan ................... 62-59934

[51] Int. Cl.$^5$ ................ A01N 31/00; C07J 9/00; C07J 41/00
[52] U.S. Cl. ................ 71/112; 71/114; 71/122; 71/123; 552/553; 552/554
[58] Field of Search .......... 514/178; 71/112, 114, 71/122, 123; 552/553, 554

Primary Examiner—Douglas W. Robinson
Assistant Examiner—Raymond J. Henley, III
Attorney, Agent, or Firm—Henry C. Nields

[57] ABSTRACT

Disclosed herein is a novel steroids represented by the formula (1):

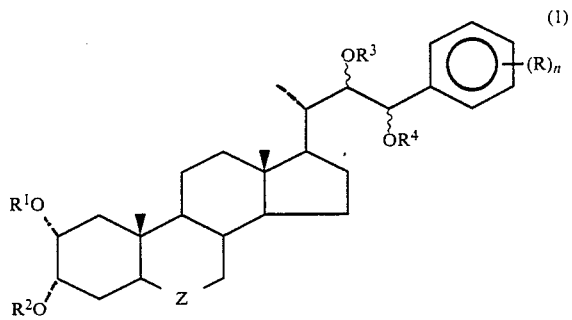

wherein
Z represents

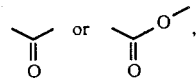

n is integer of 1 to 3,
R represents hydrogen, halogen, $CF_3$, lower alkyl, lower alkoxy or $-CO_2R'$, wherein $R'$ represents hydrogen, alkali metal or lower alkyl, and
$R^1$, $R^2$, $R^3$ and $R^4$ represent hydrogen or acyl, respectively.

The compound of the formula (1) of the present invention exhibits high durability as well as excellent plant growth regulation.

5 Claims, No Drawings

23-PHENYLSTEROIDS

This application is a division, of application Ser. No. 07/163,526, filed Mar. 3, 1988 now U.S. Pat. No. 4,886,544.

DETAILED DESCRIPTION OF THE INVENTION:

The present invention relates to a novel steroids which is useful as a plant-growth regulator, and to a preparing process thereof.

Brassinosteroids as a plant-growth regulator, were recently remarked very much owing to their extremely strong physiological activity. Their effects vary widely according to the kind and stereoisomerism of their side chains, so the synthetic research of their derivatives has been actively conducted.

For example, according to the Japanese Patent Laid-Open No. 227900/1984, 26,27-bisnorbrassinosteroid which has not two methyl groups in 26- and 27-positions of brassinolide, was found to exhibit the plant-growth promoting activity as well as the brassinolides.

However, any brassinosteroid compounds substituted by phenyl, which might be expected chemically more stable, in their side chain have never discovered in any plant body, nor yet any synthetic examples were known.

The inventors of the present invention have intensively investigated to synthesize a brassinosteroid derivative which exhibit high durability of plant growth effect as well as excellent plant growth regulation.

Under these circumstances, it has been found that phenyl which is not yet used, can be successfully introduced in the side chain, and a novel brassinosteroid represented by the formula (1) mentioned below, can be easily synthesized.

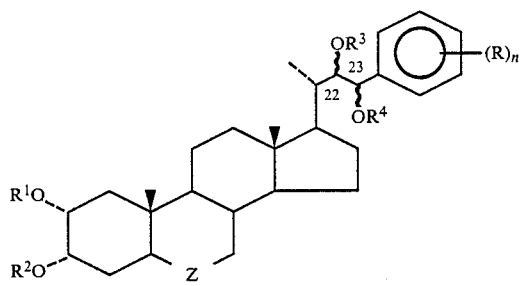

wherein
Z represents

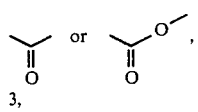

n is an integer of 1 to 3,
R represents hydrogen, halogen, $CF_3$, lower alkyl, lower alkoxy or $-CO_2R'$, wherein $R'$ represents hydrogen, alkali metal or lower alkyl, and
$R^1$, $R^2$, $R^3$ and $R^4$ represent hydrogen or acyl, respectively.

In the formula (1), steric configuration of 22-and 23-positions means one of either (22S,23S)-isomer or (22R,23R)-isomer or a mixture thereof.

The present invention will be illustrated in detail as follows.

A compound of the formula (1) of the present invention can be prepared by the process mentioned hereinafter. Namely, alkenylation (olefin synthesis, alkene formation) of a compound represented by the formula

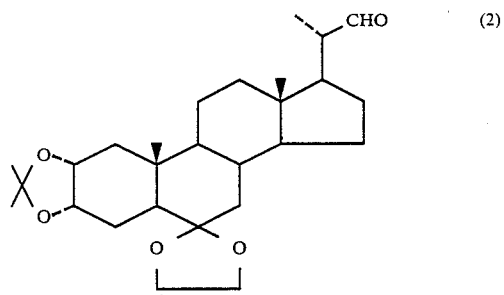

is conducted to obtain a compound represented by the formula:

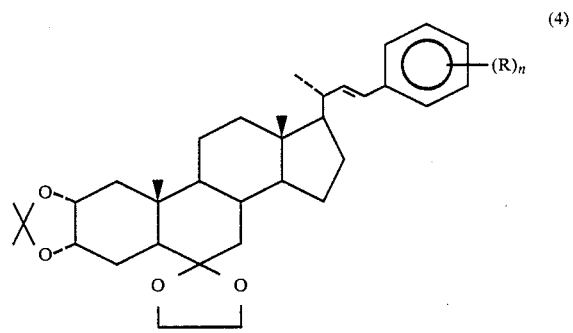

wherein R and n are as defined above. As an alkenylation, there may be mentioned, for example, the following processes.

(1) A compound of the formula (2) is reacted with a compound of the formula:

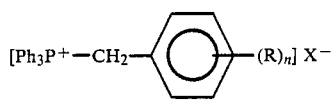

or a compound of the formula:

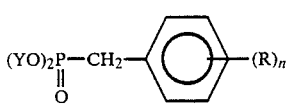

wherein
R and n are as defined above,
X represents halogen and
Y represents lower alkyl,
preferably, in molar ratio of 1:1 to 2, in the presence of base in an organic solvent, preferably at 0° to 40° C.

As organic solvents, aliphatic hydrocarbons such as n-pentane, n-hexane and heptane, ethers such as diethyl ether, tetrahydrofuran and dioxane, aromatic hydrocarbons such as benzene, toluene and monochlorobenzene, and solvent mixtures thereof may be mentioned. Among them, a solvent mixture of benzene-n-hexane is preferable.

Further, as examples of bases, organic lithium compounds such as methyl lithium, n-butyl lithium and phenyl lithium, lithium amide of dialkylamine such as LDA (lithium diisopropyl amine), potassium t-butoxide and sodium hydride may be mentioned. Among them, n-butyl lithium is preferable. Preferable amount used of base is 1 to 1.5 molar ratio to 1 mol of the compound of the formula (3) or (3)'. The reaction temperature is, for example, from −78° C. to the boiling point of the solvent, preferably near room temperature.

The alkenylation which uses the compound of the formula (3) is known as Wittig reaction and the one which uses the compound of the formula (3)' is known as Horner-Emmons reaction [J.I.G. Cadgan "Organic reagent" in Organic Synthesis, Academic Press, 155, N.Y., (1979)].

(2) The compound of the formula (4) is also obtained by reacting the compound of the formula (2) with, for example,

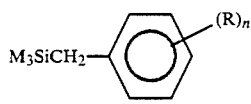

wherein
M represents lower alkyl or phenyl,
R and n are defined as above,
in the presence of alkyl lithium such as $C_2H_5Li$, $n-C_3H_7Li$ or $n-C_4H_9Li$ in an organic solvent such as aliphatic or aromatic hydrocarbon (for example, n-hexane ethylene dichloride, benzene, toluene), ether (for example, diethyl ether, tetrahydrofuran, dioxane), dimethylformaldehyde or HMPA.

A compound represented by the formula (2), as a starting material, may be obtained by known method, for example, the method similar to the reference example described in Tetrahedron, 38, p. 2099 (1982).

A compound of the formula

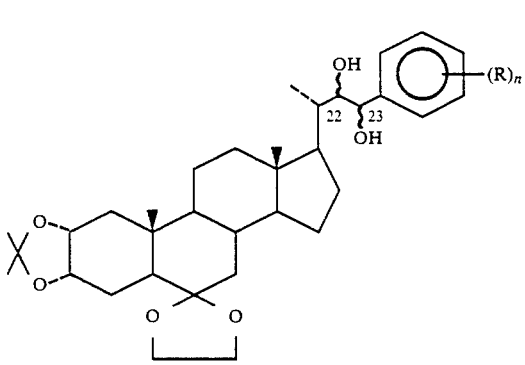

wherein R and n are as defined above, which consist of (22S-, 23S)-isomers as main products, can be obtained by oxidizing the compound of the formula (4). The oxidation may be preferably conducted using catalytic amount of osmium tetroxide in the presence of a tertiary amine N-oxide such as N-methylmorpholine-N-oxide (NMO), or pyridine in an inert solvent. As an inert solvent there may be mentioned the solvent which are used when the compound of the formula (4) is produced. The preferable molar ratio is 1 to 2 mol of osmium tetroxide per 1 mol of the compound of the formula (4). The oxidation temperature is preferably from room temperature to 70° C. In the present invention, method of oxidation is not limited to the one mentioned above. Any oxidation method that produces cis-glycol may be used.

Next, the compound of the formula (5) can be hydrolysed preferably by acid catalysts, preferably at room temperature to 100° C. to split off the protecting group such as ethylene dioxide or acetonide groups, being converted to a compound represented by the formula (6).

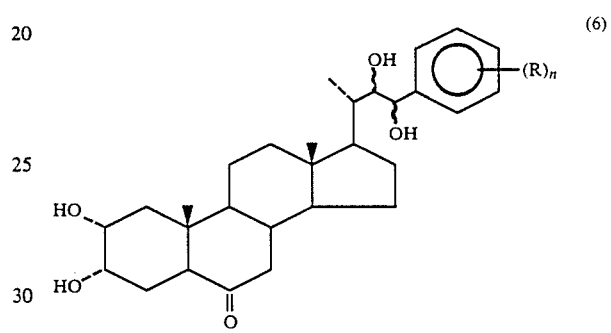

wherein R and n are as defined above.

As examples of the acid catalyst, dilute hydrochloric acid, dilute sulfuric acid, acetic acid or trifluoroacetic acid may be mentioned. Usually, dilute hydrochloric acid or acetic acid is preferable.

Then, a compound of the formula

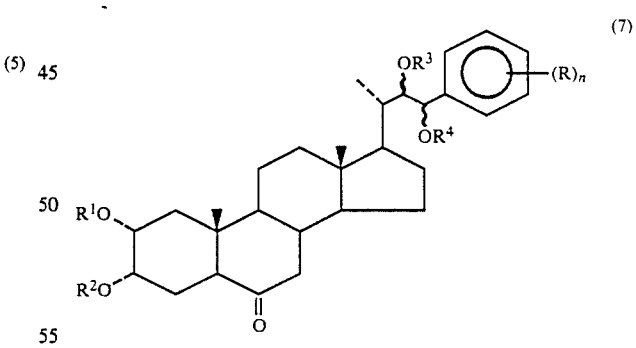

wherein R, $R^1$, $R^2$, $R^3$, $R^4$ and n are as defined above, can be obtained by reacting a compound of the above formula (6) with about 1 to 4 mol of acid anhydride or acid halide, such as acetic anhydride, trifluoroacetic anhydride, propionic acid anhydride, acetyl chloride, preferably, in the presence of bases such as pyridine etc., at temperatures preferably from 0° C. to room temperature. Subsequently, a lactone compound of the formula

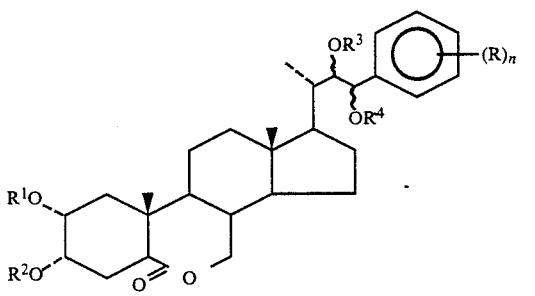

(8)

wherein R, $R^1$, $R^2$, $R^3$, $R^4$, and n are as defined above, can be derived by conducting lactonization of a compound of the formula (6) or (7).

As the lactonization method, Baeyer-Villiger reaction may be preferable. Baeyer-Villiger reaction may be performed in similar manner to the usual oxidation reaction using various organic peroxides.

For example, a compound of the formula (6) or (7) may be reacted with organic peracids such as trifluoroperacetic acid, monoperoxy phthalic acid and m-chloroperbenzoic acid, if necessary, in an organic solvent stable to oxidation, such as dichloromethane and perchloroethylene, at a low temperature, preferably −5° C. to 10° C.

As for an organic peracid, the trifluoroperacetic acid prepared in situ from trifluoroacetic anhydride and hydrogen peroxide may be used most preferably.

In addition, a compound of the formula (8) wherein $R^1$, $R^2$, $R^3$ and $R^4$ are acyl groups, can be hydrolyzed as usual as in the presence of bases to free hydroxy groups, respectively.

In the formula (1), as an example of halogen there may be mentioned F, Cl, Br or I, as an example of lower alkyl there may be mentioned methyl, ethyl, propyl, butyl, as an example of lower alkoxy, there may be mentioned methoxy, ethoxy or propoxy. As an acyl there may be mentioned acetyl, trifluoroacetyl or propionyl.

The present invention, a result of iterated original investigations, has succeeded in synthesizing easily a novel plant-growth regulating steroidal compound, which has neither been ever isolated from any plants, nor the existence in plant bodies of which has been ever known, and much less any synthesis thereof, by a very short processes. Said steroidal compound may be used to apply to plants for agriculture and horticulture as a plant growth regulator. For example, it can be utilized to regulate growth of graminaceous crops (cereals) such as rice, wheat and corn, vegetables such as tomato, cabbage, cauliflower and cucumber, fruit-trees such as grape and apple, beans such as soy bean and bush bean, coffee and cocoas.

In accordance with the invention, a steroidal compound of the formula (1) can be used either alone or in the admixture of two or more of said derivatives by dilution with water in low concentration. Alternatively, they may be mixed with adjuvants to make formulations such as dust, granule, grain, wettable powder, flowable suspension and emulsion concentrate by means of usual procedures in the agrochemical manufacture, to promote or stabilize the effect of said derivatives.

Those adjuvants mentioned above include carriers (diluents) and other adjuvants such as spreaders, emulsifiers, wetting agents, dispersing agents, fixing agents and disintegrators.

As liquid carriers there can be mentioned aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetable oils, fatty acids and their esters, etc.

As solid carriers there are mentioned clay, kaolin, talc, diatomaceous earth, silica, calcium carbonate, montmorillonite, bentonite, feldspar, quartz, alumina, sawdust, etc.

As emulsifiers or dispersing agents, surfactants are generally used. They include anionic, cationic, nonionic and amphoteric surfactants such as sodium higher alkylsulfates, stearyltrimethylammonium chloride, polyoxyethylenealkylphenyl ether, lauryl betaine, etc.

In the case of use of those carriers, it is important to scrutinize carefully and employ those which are the most suitable for promoting the efficacy of the brassinolide derivatives.

Any of said formulations can be not only alone, but also may be mixed with fungicides, insecticides, plant growth regulators, acaricides, horticultural pesticides, soil disinfectants, soil improvement agents or nematocides, and further can be used in combination with fertilizers or other herbicides.

The content of a steroidal compound of the formula (1) as active ingredient in the composition varies with types of formulation, methods of applications and other conditions, and generally it is 0.01 to 95 weight %, preferably 0.01 to 50 weight %, though sometimes the active compound may be used alone.

A plant growth regulating composition of the present invention can be applied to stem, leaf, seed or root, etc. of said plants, plant cultivation soil or plant cultivation media. In the present invention the term "apply" can include "spread", "spray", "sprinkle" or "soak".

It has been remarkably demonstrated that a steroidal compound of the formula (1) in the present invention have plant growth regulating effect even in very small amounts, and the amount applied is generally 0.00001 to 100 mg/are, preferably 0.01 to 10 mg/are. When they are applied as a solution or dispersion in water or an organic solvent, 0.0001 to 10 ppm is preferable.

When applying the composition of the invention for increasing the yield of cereals, it may be preferable to carry out the applying treatment at about the time of flowering of said crops. As used herein, the phrase "at about the time of flowering" means the period from the beginning of formation of reproductive cells to the ripening of seeds by completion of fertilization. Taking rice as an example, said period is from the filling of the ears to the harvest after finishing fertilization of the last grain flower in the ear.

The present invention will be further illustrated in detail by following examples.

SYNTHESIS EXAMPLE

SYNTHESIS EXAMPLE 1

A hexane solution of n-butyl lithium (1.6M, 1.9 ml, 3.04 mmol) was added dropwise to a solution of 1.18 g of benzyltriphenylphosphonium chloride in 10 ml of anhydrous benzene in nitrogen atmosphere at room temperature, and stirred for 20 min. Then, a solution of 1.0 g (2.24 mmol) of (2R, 3S, 20S)-2,3-isopropylidenedioxy-6,6-ethylenedioxy-20-formyl-5α-pregnan in 6 ml of benzene was added dropwise thereto, and reacted at room temperature for 1 hour. After the reaction mixture was filtered to remove the insoluble precipitate, the organic layer thereof was separated by adding water, washed with a saturated aqueous solution of common salt, and dried over anhydrous magnesium sulfate. A crude product obtained by distilling the solvent away under reduced pressure, was purified by means of a silica-gel column chromatography (eluent: benzene/ethyl acetate) to give 0.86 g (yield 72%) of 6,6-ethylenedioxy-2α,3α-isopropylidenedioxy-23-phenyl-5α,24-norchol-22E-ene (the compound of the formula (4) wherein R=H)

$^1$H NMR (CDCl$_3$), δ0.73 (s, 3H, 18-CH$_3$), 0.84 (s, 3H, 19-CH$_3$), 1.11 (d, 3H, 21-CH$_3$), 1.32 (s, 3H, acetonide), 1.47 (s, 3H, acetonide), 3.8 to 4.3 (6H, m,

—O—(CH$_2$)$_2$—O— + 2β-H + 3β-H), 6.01 (dd, J=15.4 and 7.7 Hz, 1H, 23-H), 6.30 (d, J=15.4 Hz, 1H, 22-H), 7.2 to 7.4 (m, 5H, C$_6$H$_5$).

SYNTHESIS EXAMPLE 2

0.69 g (1.3 mmol) of 6,6-ethylenedioxy-2α,3α-isopropylidenedioxy-23-phenyl-5α,24-norchol-22E-ene was dissolved in 4.8 ml of THF, added with 16 ml of t-butanol and 0.8 ml of water, and stirred well. Next, 0.01 g of osmium tetroxide was added thereto, then also 2.0 g of 60% N-methylmorpholin-N-oxide (NMO), and the reaction was traced by means of TLC. Further, 0.01 g of osmium tetroxide and 4.0 g of 40% NMO were added thereto to accomplish the reaction. 75 ml of saturated solution of sodium hydrogen sulfite was added to the reaction mixture, and after stirring for a while the mixture was filtered through Celite, extracted by methylene chloride, and the extract was dried over magnesium sulfate. A crude product obtained by distilling away the solvents under reduced pressure was purified by means of silica-gel column chromatography (eluent: n-hexane/ethyl acetate) to give 0.28 g (yield 38%) of 22,23-dihydroxy-6,6-ethylenedioxy-2α,3α-isopropylidenedioxy-23-phenyl-5α,24-norcholane (the compound of the formula (5) wherein R=H).

IR (cm$^{-1}$); 3430 (br, OH)

$^1$H NMR (CDCl$_3$); δ0.64 (s, 3H, 18-CH$_3$), 0.81 (s, 3H, 19-CH$_3$), 1.10 (d, 3H, 21-CH$_3$), 1.32 (s, 3H, acetonide), 1.46 (s, 3H, acetonide), 2.46 (d, J=4.9 Hz, 1H), 2.60 (d, J=5.1 Hz, 1H), 3.8 to 4.0 (m, 4H, —OCH$_2$CH$_2$O—), 4.25 (m, 1H), 4.73 (t, J=4.9 Hz, 1H), 7.34 (s, 5H, C$_6$H$_5$).

SYNTHESIS EXAMPLE 3

0.28 g (0.5 mmol) of 22,23-dihydroxy-6,6-ethylenedioxy-2α,3α-isopropylidenedioxy-23-phenyl-5α,24-norcholane and 12.5 mol of 80% acetic acid were reacted at 50° to 60° C. for 1.5 hours, and after cooling, an aqueous solution containing 9.26 g of sodium carbonate was added thereto. The mixture was extracted four times by ethyl acetate, and the extract solution was washed with a saturated aqueous solution of common salt and dried over magnesium sulfate. 0.21 g (yield 89%) of 2α,3α,22,23-tetrahydroxy-23-phenyl-5α,24-norchol-6-one (the compound of the formula (6) wherein R=H) was obtained by distilling away the solvents under reduced pressure.

IR (cm$^{-1}$); 3430 (br, OH), 1700 (C=O).

SYNTHESIS EXAMPLE 4

0.21 g (0.45 mmol) of 2α,3α,22,23-tetrahydroxy-23-phenyl-5α,24-norchol-6-one was dissolved in 3 ml of pyridine, and 0.6 g of acetic anhydride and 0.05 g of 4-(N,N-dimethylamino) pyridine were added thereto. After reacted at room temperature for 20 hours, the mixture was poured into an ice water containing dilute hydrochloric acid. It was extracted three times with ethyl acetate, and the extract solution was washed with a saturated aqueous solution of sodium bicarbonate, and further with a saturated aqueous solution of common salt, then dried over magnesium sulfate. 0.29 g (quantitative yield) of 2α,3α,22,23-tetraacetoxy-23-phenyl-5α,24-norchol-6-one (the compound of the formula (7) werein R$^1$-R$^4$=acetyl and R=hydrogen) was obtained by distilling away the solvents in reduced pressure.

IR (cm$^{-1}$); 1780 (COCH$_3$), 1700 (C=O).

SYNTHESIS EXAMPLE 5

3 ml of methylene chloride solution of trifluoro peracetic acid (prepared from 1.0 g of 35% hydrogen peroxide and 1.6 ml of trifluoroacetic anhydride at 0° C.) was added to 0.28 g (0.44 mmol) of 2α,3α,22,23-tetraacetoxy-23-phenyl-5α,24-norchol-6-one, 1.28 g of Na$_2$HPO$_4$ and 15 ml of methylene chloride, and the reaction temperature was restored to room temperature. Then the mixture was reacted by boiling under reflux for 5 hours. By adding an ice water thereto after cooling, methylene chloride layer was separated, and water layer was extracted well with methylene chloride. Both methylene chloride layer was gathered together, and washed with a saturated aqueous solution of common salt, then dried over magnesium sulfate. 0.27 g of a crude product was obtained by distilling away the solvent under reduced pressure, and was purified by means of column chromatography (SiO$_2$, eluent: n-hexane/ethyl acetate=1/5) to give 0.07 g of a mixture of (22R,23R)-2α,3α,22,23-tetraacetoxy-23-phenyl-B-homo-7-oxa-5α,24-norchol-6-one and (22S,23S)-2α,3α,22,23-tetraacetoxy-23-phenyl-B-homo-7-oxa-5α,24-norchol-6-one [IR(cm$^{-1}$): 1740 (br, CH$_3$CO+

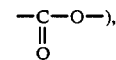
—C—O—),
‖
O $^1$H NMR (CDCl$_3$); δ 1.988 (s, Ac), 2.001 (s, Ac), 2.069 (s, Ac), 2.113 (s, Ac), 2.126 (s, Ac), 2.167 (s, Ac), 7.33 (s, C$_6$H$_5$)] and 0.13 g (yield: 45%) of (22S,23S)-2α,3α,22,23-tetraacetoxy-23-phenyl-B-homo-7-oxa-5α,24-norchol-6-one [$^1$H NMR (CDCl$_3$); δ 1.991 (s, 3H, Ac), 2.001 (s, 3H, Ac), 2.074 (s, 3H, Ac), 2.116 (s, 3H, Ac), 3.0 (dd, 1H, 5α-H), 4.0 to 4.1 (m, 2H, 7-CH$_2$), 4.88 (m, 1H, 2β-H), 5.17 (dd, 1H, 22 (or 23)-H, 5.37 (br, 1H, 3β-H), 6.03 (d, 1H, 23 (or 22)-H), 7.33 (s, 5H, C$_6$H$_5$)].

SYNTHESIS EXAMPLE 6

0.2 g of 2α,3α,22,23-tetraacetoxy-23-phenyl-B-homo-7-oxa-5α,24-norchol-6-one was dissolved in 15 ml of methanol, and 1 ml of aqueous solution of 0.42 g of NaOH was added dropwise thereto, then they were reacted by boiling under reflux for 3 hours. After cooling, the reaction mixture was added with 4.3 ml of 6N-hydrochloric acid and 15 ml of THF, and stirred at room temperature for 3 hours. After distilling away the solvents under reduced pressure, the residue was neutralized by adding 1.83 g of NaHCO$_3$ powder, and extracted with chloroform three times. After washing by a saturated aqueous solution of common salt, the extract solution was dried over sodium sulfate, and the solvents were distilled away to give 0.134 g (yield 94%) of 2α,-3α,22,23-tetrahydroxy-23-phenyl-B-homo-7-oxa-5α,24-norchol-6-one (a compound of the formula (8) wherein R=H and $R^1-R^4$=H), which was a mixture of (22S,23S)-2α,3α,22,23-tetrahydroxy-23-phenyl-B-homo-7-oxa-5α,24-norchol-6-one and (22R,23R)-2α,-3α,22,23-tetrahydroxy-23-phenyl-B-homo-7-oxa-5α,24-norchol-6-one.

IR and $^1$H NMR showed the following results.

IR (cm$^{-1}$); 3420 (br, OH), 1710 (CO)

$^1$H NMR (CDCl$_3$+DMSO-d$_6$); δ 0.63 (s), 0.64 (s), 0.89 (s), 1.00 (d), 3.1 (dd), 3.3 (d), 3.55 to 3.8 (m), 3.95 to 4.1 (m), 4.65 (m), 7.33 (s).

This mixture was purified by means of silica-gel column chromatography (eluent: chloroform/methanol=15/1) to give 28 mg of (22S,23S)-2α,3α,22,23-tetrahydroxy-23-phenyl-B-homo-7-oxa-5α,24-norchol-6-one, m.p. 146° to 149° C.

This compound showed the following results of IR and $^1$H NMR.

IR (cm$^{-1}$); 3400 (br, OH), 1715 (C=O).

$^1$H NMR (CDCl$_3$); δ 0.66 (s, 3H, 18-CH$_3$), 0.88 (s, 3H, 19-CH$_3$), 1.10 (d, 3H, 21-CH$_3$), 3.08 (dd, 1H, 5α-H), 3.55 to 3.8 (m, 3H), 3.95 to 4.05 (m, 2H, 7-CH$_3$), 4.7 (m, 1H), 7.35 (s, 5H, C$_6$H$_5$).

EI-MS (tetrakistrimethylsilyl compound); m/z 774 (M$^+$), 759 (M$^+$-CH$_3$), 668, 595 (base, M$^+$-179, C$_{22}$-C$_{23}$ fission), 505, 463, 415, 375, 357, 325, 285, 227, 179, 147. Calcd. for C$_{41}$H$_{74}$O$_6$Si$_4$ 775, 387.

SYNTHESIS EXAMPLE 7

50 ml of anhydrous benzene was added to a mixture of 8.82 g (3.36×10$^{-2}$ mol) of diethyl p-chlorobenzylphosphonate which was obtained by reacting triethyl phosphite with p-chlorobenzylchloride and 5.00 g (11.2 mmol) of (2R,3S,20s)-2,3-isopropylidenedioxy-6,6-ethylenedioxy-20-formyl-5α-pregnan. 1.34 g (3.35×10$^{-2}$ mol) of sodium hydride (60%) was added to the above solution and allowed to react for three days at room temperature. Another 8.82 g of diethyl p-chlorobenzylphosphonate was added thereto and allowed to react for one day to complete the reaction.

After the reaction, reaction solution was washed with a saturated aqueous solution of common salt and dried over anhydrous magnesium sulfate. A crude product obtained by distilling away the solvent under reduced pressure, was purified by means of silica gel column chromatography (eluent: hexane/ethyl acetate) to give 4.66 g of 6,6-ethylenedioxy-2α,3α-isopropylidenedioxy-23-p-chlorophenyl-5α,24-norchol-22E-ene.

$^1$H NMR (CDCl$_3$); δ 0.72 (s, 3H, 18-CH$_3$), 0.95 (s, 3H, 19-CH$_3$), 1.07 (d, 3H, 21-CH$_3$), 1.32 (s, 3H, acetonide), 1.47 (s, 3H, acetonide), 3.8 to 4.3 (m, 6H,

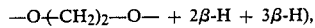

6.0 to 6.2 (m, 2H, 22-H, 23-H), 7.23 (s, 4H, C$_6$H$_4$)

SYNTHESIS EXAMPLE 8

4.66 g (8.4 mmol) of 6,6-ethylenedioxy-2α,3α-isopropylidenedioxy-23-p-chlorophenyl-5α,24-norchol-22E-ene was dissolved into 42.9 ml of tetrahydrofuran, 142.9 ml of t-butanol and 14.3 ml of water were added and stirred well. Then 128 mg of osmium tetroxide, 3.41 g of N-methyl-morphorine-N-oxide were added thereto and allowed to react for a few days. A saturated solution of sodium hydrogen sulfide was added to the reaction mixture and after stirring for a while, the mixture was filtered through celite, extracted by methylene chloride. After washing with water, the extract was dried over anhydrous magnesium sulfate. A crude product extract obtained by distilling away the solvent under reduced pressure was purified by means of silica gel column chromatography (eluent: n-hexane/ethyl acetate) to obtain 3.40 g of 22,23-dihydroxy-6,6-ethylenedioxy-2α,3α-isopropylidenedioxy-23-p-chlorophenyl-5α,24-norcholane.

$^1$H NMR (CDCl$_3$); δ 0.61 (18-CH$_3$), 0.66 (18-CH$_3$), 0.82 (19-CH$_3$), 1.34 (acetonide), 1.46 (acetonide), 3.5 to 4.0 (—OCH$_2$CH$_2$O—), 4.25 (m), 4.68 (m), 7.31 (s, benzene ring proton).

SYNTHESIS EXAMPLE 9

3.30 g (5.6 mmol) of 22,23-dihydroxy-6,6-ethylenedioxy-2α,3α-isopropylidenedioxy-23-p-chlorophenyl-5α,24-norcholane was allowed to react with 60 ml of 80% acetic acid for 2 hours at 50° to 60° C. After cooling, the reaction solution was extracted with a mixed solvent of butanol and ethyl acetate, the obtained extract was washed with an aqueous solution of sodium carbonate, a saturated aqueous solution of common salt and dried over anhydrous magnesium sulfate. 2.79 g of 2α,3α,22,23-tetrahydroxy-23-p-chlorophenyl-5α,24-norchol-6-one was obtained after distilling off the solvent under reduced pressure. The above compound was a mixture of (22S,23S) and (22R,23R)-tetraol. The mixed compounds were purified by means of silica gel column chromatography (eluent: chloroform:ethanol:ammonia water=100:3:0.3) to obtain 1.1 g of (22S,23S)-2α,3α,22,23-tetrahydroxy-23-p-chlorophenyl-5α,24-norchol-6-one and 0.56 g of (22R,23R)-2α,-3α,22,23-tetrahydroxy-23-p-chlorphenyl-5α,24-norchol-6-one.

(22S,23S)-isomer
m.p.: 179°–181° C.

$^1$H NMR (CDCl$_3$+DMSO-d$_6$); δ 0.65 (18-CH$_3$), 0.71 (19-CH$_3$), 3.55 (m), 3.83 (dd), 3.97 (d), 4.11 (d), 4.61 (m), 4.75 (d), 7.31 (s, benzene ring).

(22R,23R)-isomer
m.p.: 126°–128° C.

$^1$H NMR (CDCl$_3$+DMSO-d$_6$); δ 0.61 (18-CH$_3$), 0.72 (19-CH$_3$), 3.4 to 4.0 (m), 4.62 (m), 4.71 (d), 7.31 (s, benzene ring).

SYNTHESIS EXAMPLE 10

60 ml of a mixture of acetic anhydride and pyridine (1:9) was added to 0.83 g of (22S,23S)-2α,3α,22,23-tetrahydroxy-23-p-chlorophenyl-5α,24-norchol-6-one and allowed to react for one day at 50° C. After completing the reaction, the reaction mixture was extracted with ethyl acetate, the extract was washed with diluted aqueous solution of hydrochloric acid, saturated aqueous solution of sodium carbonate and saturated aqueous solution of common salt, dried over anhydrous magnesium sulfate. The solvent was distilled off under reduced pressure to give 0.94 g of (22S,23S)-2α,3α,22,23-tetraacetoxy-23-p-chlorophenyl-5α,24-norchol-6-one.

m.p.: 128°–130° C.

$^1$H NMR (CDCl$_3$); δ 0.63 (18-CH$_3$), 0.81 (19-CH$_3$), 2.01 (Ac), 2.04 (Ac), 2.08 (Ac×2), 4.02 (dd), 4.89 (m), 5.14 (m), 5.28 (m), 6.0 (d), 7.30 (s, benzene ring).

0.52 g of (22R,23R)-2α,3α,22,23-tetrahydroxy-23-p-chlorophenyl-5α,24-norchol-6-one was acetylated in a similar manner as above to give 0.59 g of (22R,23R)-2α,-3α,22,23-tetraacetoxy-23-p-chlorophenyl-5α,24-norchol-6-one.

m.p.: 258°–260° C.

¹H NMR (CDCl₃); δ 0.64 (18-CH₃), 0.83 (19-CH₃), 2.00 (Ac), 2.02 (Ac), 2.08 (Ac), 2.10 (Ac), 4.12 (dd), 4.94 (m), 5.20 (m), 5.38 (m), 6.0 (d), 7.30 (s, benzene ring).

SYNTHESIS EXAMPLE 11

Trifluoroperacetic acid was prepared by reacting 0.41 ml of 60% hydrogen peroxide with 2.41 ml of trifluoroacetic anhydride in 10 ml of methylene chloride at 0° C. The whole trifluoroperacetic acid obtained as above was added to a solution of 0.705 g (1.0 mmol) of (22S,23S)-2α,3α,22,23-tetraacetoxy-23-p-chlorophenyl-5α,24-norchol-6-one, 1.05 g of Na₂HPO₄ and 50 ml of methylene chloride and allowed to react at 0° C. Then, the temperature of the reaction mixture was raised to room temperature and allowed to react under refluxing for 3 hrs. After the reaction, the reaction mixture was washed with an aqueous solution of common salt, dried over anhydrous magnesium sulfate and the solvent was distilled off under reduced pressure to give 0.733 g of crude product.

The crude product was purified by silica gel column chromatography (eluent: benzen/ethyl acetate) to obtain 559 mg of (22S,23S)-2α,3α,22,23-tetraacetoxy-23-p-chlorophenyl-B-homo-7-oxa-5α,24-norchol-6-one. Similarly, 0.54 g of (22R,23R)-2α,3α,22,23-tetraacetoxy-23-p-chlorophenyl-5α,24-norchol-6-one was oxidized and resulting crude product was purified to obtain 421 mg of (22R,23R)-2α,3α,22,23-tetraacetoxy-23-p-chlorophenyl-B-homo-7-oxa-5α,24-norchol-6-one.

(22S,23S)-isomer m.p.: 159°–161° C.

¹H NMR (CDCl₃); δ 0.66 (18-CH₃), 0.96 (19-CH₃), 1.99 (Ac), 2.00 (Ac), 2.07 (Ac), 2.11 (Ac), 3.00 (dd), 4.0 to 4.17 (m), 4.87 (m), 5.12 (m), 5.37 (m), 6.00 (d), 7.29, 7.35 (benzene ring).

(22R,23R)-isomer m.p.: 133°–135° C.

¹H NMR (CDCl₃); δ 0.67 (18-CH₃), 0.98 (19-CH₃), 2.01 (Ac×2), 2.07 (Ac), 2.13 (Ac), 3.00 (dd), 4.05 to 4.15 (m), 4.88 (m), 5.20 (m), 5.38 (m), 5.97 (d), 7.30, 7.36 (benzene ring).

SYNTHESIS EXAMPLE 12

430 mg of (22S,23S)-2α,3α,22,23-tetraacetoxy-23-p-chlorophenyl-B-homo-7-oxa-5α,24-norchol-6-one was dissolved in 30 ml of 1N KOH aqueous methanol solution and allowed to react under reflux for three hours. After cooling, 20 ml of 2N hydrochloric acid and 50 ml of mixed solvent (butanol-acetic acid were added to the above reaction mixture and stirred at room temperature for three hours. After the usual operation, 300 mg of crude product was obtained and the crude product was purified by silica gel column chromatography (eluent: chloroform:ethanol:methanol=100:2:1) to obtain 150 mg of (22S,23S)-2α,3α,22,23-tetrahydroxy-23-p-chlorophenyl-B-homo-7-oxa-5α,24-norchol-6-one. Similarly, 102 mg of (22R,23R)-2α,3α,22,23-tetrahydroxy-23-p-chlorophenyl-B-homo-7-oxa-5α,24-norchol-6-one from 270 mg of (22R,23R)-2α,3α,22,23-tetraacetoxy-23-p-chlorophenyl-5α-24-norchol-6-one.

(22S,23S)-isomer

¹H NMR (CDCl₃+DMSO-d₆); δ 0.67 (s, 3H, 18-CH₃), 0.83 (s, 3H, 19-CH₃), 3.10 (dd, 1H, 5α-H), 3.4–3.65 (m, 3H), 3.8–4.1 (m), 4.15 (m), 4.58 (m), 4.81 (d, 1H, 23-H), 7.31 (s, 4H, benzene ring).

m.p.; 213°–214° C.

(22R,23R)-isomer

¹H NMR (CDCl₃+DMSO-d₆); δ 0.63 (s, 3H. 18-CH₃), 0.85 (s, 3H, 19-CH₃), 3.13 (dd, 1H, 5α-H), 3.3–3.65 (m), 3.7–4.2 (m), 4.60 (m), 4.80 (m), 7.31 (s, 4H, benzene ring).

m.p.; 246°–248° C.

Representative compounds of the present invention, which were prepared according to the process for preparation similar to the procedure in above Synthesis Examples are shown in Table 1.

TABLE 1

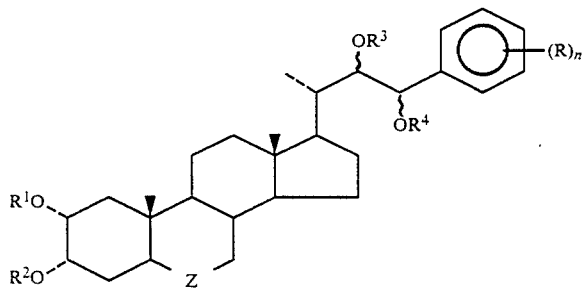

(1)

| Compound No. | R¹ | R² | R³ | R⁴ | Configuration of 22- and 23- | R | n | Z | IR(cm⁻¹) or ¹H NMR (CDCl₃+ DMSO-d₆) or m.p. |
|---|---|---|---|---|---|---|---|---|---|
| 1 | H | H | H | H | (22S,23S) | H | 1 | –O–C(=O)– | shown in Synthesis Example 6 |
| 2 | " | " | " | " | mixture of (22S,23S) and (22R,23R) | H | 1 | " | " |
| 3 | COCH₃ | COCH₃ | COCH₃ | COCH₃ | (22S,23S) | " | " | " | Shown in Synthesis Example 5 |
| 4 | " | " | " | " | mixture of (22S,23S) and (22R,23R) | " | " | " | " |

TABLE 1-continued

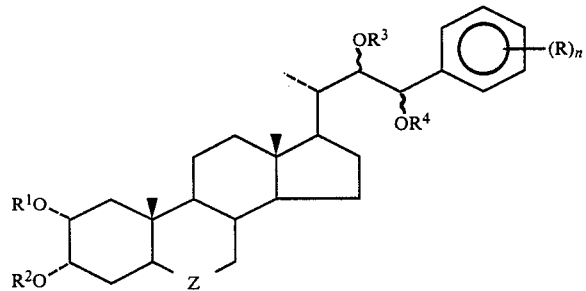
(1)

| Compound No. | $R^1$ | $R^2$ | $R^3$ | $R^4$ | Configuration of 22- and 23- | R | n | Z | IR(cm$^{-1}$) or $^1$H NMR (CDCl$_3$ + DMSO-d$_6$) or m.p. |
|---|---|---|---|---|---|---|---|---|---|
| 5 | H | H | H | H | mixture of (22S,23S) and (22R,23R) | H | 1 | ⟩=O | shown in Synthesis Example 3 |
| 6 | COCH$_3$ | COCH$_3$ | COCH$_3$ | COCH$_3$ | " | " | " | ⟩=O | shown in Synthesis Example 4 |
| 7 | H | H | H | H | (22R,23R) | P-Cl | 1 | —C(=O)—O— | shown in Synthesis Example 12 |
| 8 | H | H | H | H | (22S,23S) | P-Cl | 1 | —C(=O)—O— | shown in Synthesis Example 12 |
| 9 | H | H | H | H | (22S,23S) | P-Cl | 1 | ⟩=O | $^1$HNMR δ0.65(s,3H,18-CH$_3$), 0.71(s,3H,19-CH$_3$) 2.65(dd, 5α-H), 3.45–3.7(m) 3.83(dd), 4.11(dd) 4.61(m), 4.75(d,1H) 7.31(s, 4H, benzene ring) |
| 10 | H | H | H | H | (22R,23R) | m-Cl | 1 | —C(=O)—O— | IR: 3410(br, OH) 1710(CO) $^1$HNMR:δ0.62(S,3H,18-CH$_3$) 0.89(S,3H, 19-CH$_3$) 3.1(d,d,1H,5α-H) 3.6–3.8(m,3H) 3.9–4.1(m,2H) 4.67(m,1H) 7.2–7.4(m,4H, benzene ring) |
| 11 | " | " | " | " | (22S,23S) | 2,4-di-Cl | 2 | —C(=O)—O— | IR: 3460(br, OH) 1710(CO) $^1$HNMR:δ0.67(3H, 18-CH$_3$) 0.93(3H, 19-CH$_3$) 3.11 (d,d, 1H, 5α-H) 3.6–3.8(m, 3H) 4.07(m, 2H, 7-CH$_2$) 4.85(m, 1H, 23-H) 7.05(m, 2H, benzene ring) 7.30(m, 1H, benzene ring) |
| 12 | " | " | " | " | (22S,23S) | p-COOH | 1 | —C(=O)—O— | IR: 3420(br, OH), 2750(br, OH) 1725(CO), 1705(CO) $^1$HNMR:δ0.65(3H, 18-CH$_3$) 0.92(3H, 19-CH$_3$) 3.20(d,d, 1H, 5α-H) 3.6–3.8(m, 3H) 4.09(m, 2H, 7-CH$_2$) 4.75(m, 1H ) 7.20(2H, benzene ring) 7.90(2H, benzene ring) |

TABLE 1-continued (1)

| Compound No. | R¹ | R² | R³ | R⁴ | Configuration of 22- and 23- | R | n | Z | IR(cm⁻¹) or ¹H NMR (CDCl₃+ DMSO-d₆) or m.p. |
|---|---|---|---|---|---|---|---|---|---|
| 13 | H | H | H | H | (22R,23R) | p-COOCH₃ | 1 | —O—C(=O)—CH₃ | IR: 3415(br, OH) 1735(CO), 1710(CO) ¹HNMR:δ0.66(3H, 18-CH₃) 0.95(3H, 19-CH₃) 3.15(d,d, 1H, 5α-H) 3.6–3.8(m, 3H) 3.65(S, 3H, —CO₂C$\underline{\text{H}}$₃) 4.08(m, 2H, 7-CH₂) 4.75(m, 1H) 7.1(m, benzene ring) 8.08(m, benzene ring) |
| 14 | " | " | " | " | (22S,23S) | m-COOH | 1 | —O—C(=O)—CH₃ | IR: 3420(br, OH), 2600(br, OH) 1730(CO), 1710(CO) ¹HNMR:δ0.65(3H, 18-CH₃) 0.95(3H, 19-CH₃) 3.11(d,d, 1H, 5α-H) 3.6–3.8(m, 3H) 4.10(m, 2H, 7-CH₂) 4.85(m, 1H) 7.25(m, 4H, benzene ring) 7.74(m, 4H, benzene ring) |
| 15 | " | " | " | " | (22S,23S) | p-Br | 1 | —C(=O)—CH₃ | ¹H NMR: δ 0.66 (s, 3H, 18-CH₃) 0.74 (s, 3H, 19-CH₃) 2.68 (dd, 1H, 5α-H) 3.6–3.85 (m), 3.95–4.1 (m), 4.65–4.75 (m), 7.23 (d, 2H, benzene ring), 7.48 (d, 2H, benzene ring) |
| 16 | H | H | H | H | (22S,23S) | p-Br | 1 | —O—C(=O)—CH₃ | m.p.: 222–222.5° C. ¹H NMR: δ 0.67 (s, 3H, 18-CH₃), 0.86 (S, 3H, 19-CH₃), 3.12 (dd, 1H, 5α-H), 3.4 –3.7 (m), 3.8–4.16 (m), 4.60 (m, 1H), 4.71(d, 1H), 7.26(d,2H, benzene ring), 7.47 (d, 2H, benzene ring) |
| 17 | " | " | " | " | mixture of *22S,23S) and (22R,23R) | 2,4,5-tri-Cl | 3 | —O—C(=O)—CH₃ | IR: 3410(br, OH) 1705(CO) ¹HNMR: δ3.1(d,d,), 3.2(d,d) (CDCl₃) 4.7–4.85(m) 7.2–7.35(m, benzene ring) |
| 18 | " | " | " | " | (22S,23S) | p-CF₃ | 1 | —O—C(=O)—CH₃ | IR: 3450(br, OH) 1710(CO) ¹HNMR: δ0.67(3H, 18-CH₃) (CDCl₃) 0.95(3H, 19-CH₃), 3.20 (d,d, 1H, 5α-H) 3.6–3.8(m, 3H) 4.09(m, 2H, 7-CH₂) 4.90(m, 1H) 7.25(d, 2H, benzene ring) 7.48(d, 2H, benzene ring) |

TABLE 1-continued

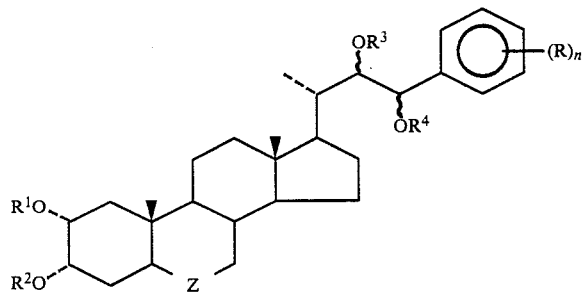

(1)

| Compound No. | R¹ | R² | R³ | R⁴ | Configuration of 22- and 23- | R | n | Z | IR(cm$^{-1}$) or $^1$H NMR (CDCl$_3$+ DMSO-d$_6$) or m.p. |
|---|---|---|---|---|---|---|---|---|---|
| 19 | H | H | H | H | (22S,23S) | p-CH$_3$ | 1 | -) | IR: 3460(br, OH), 1715 (CO)<br>$^1$HNMR: δ0.74 (3H, 18-CH$_3$)<br>0.93(3H, 19-CH$_3$)<br>2.25(3H, CH$_3$)<br>3.12(d,d, 1H, 5α-H), 3.6–3.8(m, 3H)<br>4.07(m, 2H, 7-CH$_2$)<br>4.60(m, 1H)<br>6.8(d, 2H, benzene ring)<br>7.05(d, 2H, benzene ring) |
| 20 | " | " | " | " | (22R,23R) | p-CH$_3$ | 1 | -) | IR: 3450(br, OH)<br>1715(CO)<br>$^1$HNMR: δ0.71(3H, 18-CH$_3$)<br>(CDCl$_3$) 0.93(3H, 19-CH$_3$)<br>2.30(3H, CH$_3$)<br>3.15(d,d, 1H, 5α-H)<br>3.54(m, 1H)<br>3.75(m, 1H)<br>4.1–4.2(m, 3H)<br>4.65(m, 1H)<br>7.0(m, 4H, benzene ring) |
| 21 | " | " | " | " | (22R,23R) | p-Br | 1 | -) | $^1$H NMR: δ<br>0.64 (s, 3H, 18-CH$_3$),<br>0.85 (s, 3H, 19-CH$_3$),<br>3.12 (dd, 1H, 5α-H), 3.3–3.7<br>(m), 3.8–4.2 (m), 4.58 (m, 1H),<br>4.82 (d, 1H), 7.25 (d, 2H,<br>benzene ring), 7.45 (d, 2H,<br>benzene ring)<br>m.p.: 247–249° C. |
| 22 | H | H | H | H | (22R, 23R) | 2,4-di-Cl$_2$ | 2 | -) | IR: 3460(br,OH)<br>1710(CO)<br>$^1$HNMR: δ0.74(3H, 18-CH$_3$)<br>0.95(3H, 19-CH$_3$)<br>3.12(d,d, 1H, 5α-H)<br>3.45(m, 1H)<br>3.75(m, 1H)<br>4.0–4.2(m, 3H), 4.90(m, 1H)<br>7.08(m, 2H, benzene ring)<br>7.30(m, 2H, benzene ring) |
| 23 | " | " | " | " | (22R,23R) | p-COOH | 1 | -) | IR: 3460(br, OH) 2600(br, OH)<br>1710(CO), 1705(CO)<br>$^1$HNMR: δ0.72(3H, 18-CH$_3$)<br>0.93(3H, 19-CH$_3$)<br>3.11(d.d, 1H, 5α-H)<br>3.50(m, 1H)<br>3.77(m, 1H)<br>4.1–4.2(m, 3H)<br>4.75(m, 1H)<br>7.25(d, 2H, benzene ring)<br>7.95(d, 2H, benzene ring) |

TABLE 1-continued (1)

[Structure: steroid-like compound with R¹O, R²O on left ring, OR³ and OR⁴ groups, phenyl ring with (R)ₙ substituent, and Z group]

| Compound No. | R¹ | R² | R³ | R⁴ | Configuration of 22- and 23- | R | n | Z | IR(cm⁻¹) or ¹H NMR (CDCl₃+ DMSO-d₆) or m.p. |
| --- | --- | --- | --- | --- | --- | --- | --- | --- | --- |
| 24 | " | " | " | " | (22R,23R) | p-COOCH₃ | 1 | –O–C(=O)–CH₃ | IR: 3450(br, OH), 1730(CO), 1705(CO)<br>¹HNMR: δ0.75(3H, 18-CH₃)<br>0.95(3H, 18-CH₃)<br>3.05(d,d, 1H, 5α-H)<br>3.41(m, 1H)<br>3.75(m, 1H)<br>4.0–4.2(m, 6H, —CO₂C$\underline{H}$₃)<br>4.75(m, 1H)<br>7.05(d, 2H, benzene ring)<br>8.08(d, 2H, benzene ring) |
| 25 | H | H | H | H | (22R,23R) | p-Br | 1 | C=O | ¹H NMR: δ<br>0.61 (s, 3H, 18-CH₃),<br>0.72 (s, 3H, 19-CH₃),<br>2.68 (dd, 1H, 5α-H),<br>3.35–4.0 (m), 4.5–4.7 (m),<br>7.25 (d, 2H, benzene ring),<br>7.45 (d, 2H, benzene ring) |
| 26 | H | H | H | H | (22R,23R) | p-Cl | 1 | C=O | ¹H NMR: δ<br>0.61 (s,3H, 18-CH₃),<br>0.72 (s, 3H, 19-CH₃),<br>2.68 (dd, 5α-H),<br>3.35–3.65(m), 3.8–4.0 (m),<br>4.65 (dd, 1H,), 4.71(d, 1H)<br>7.31 (s, 4H, benzene ring) |

FORMULATION EXAMPLES

FORMULATION EXAMPLE 1

Emulsion 35 parts of a mixture (1:1) of xylene and methylnaphthalene are added to a mixture of 50 parts of Compound No. 1 to form a solution and the solution is further mixed with 15 parts of a mixture (8:2) of polyoxyethylenealkylphenyl ether and calcium alkylbenzenesulfonate to obtain an emulsion.

FORMULATION EXAMPLE 2

Dust 5 parts of Compound No. 1 are mixed with 95 parts of clay and pulverized to obtain a dust.

FORMULATION EXAMPLE 3

Wettable powder 1 part of Compound No. 8 are mixed with 10 parts of diatomaceous earth and 71 parts of kaolin as the carriers and further uniformly blended with 18 parts of a mixture of sodium laurylsulfate and sodium 2,2-dinaphthylmethanesulfonate, and thereafter finely pulverized to obtain a wettable powder.

FORMULATION EXAMPLE 4

Granule 0.01 part of a fine dust of Compound No. 7 is spread and coated on 98.4 parts of grains (16 to 32 mesh) of silica to obtain a granule, by using a methanol solution of 1.5 parts of polyvinylacetate as the binding agent in a proper mixer.

TEST EXAMPLE

TEST EXAMPLE 1

Test on lamina inclination of rice plant (lamina joint)

0.5% agar was placed 2 cm deep in a plastic container, 16 cm × 16 cm × 17 cm, and on the surface of the agar, rice seeds, germinated 24 hours ago, (variety: NIHONBARE) were sown, the upper parts of which were covered by aluminium foil. Then, breeding was exercised at 30° C. in the dark for 6 days. After that, surroundings of lamina joint parts of the second leaf were cut off about 5 mm across, and the lamina joint parts were floated in a pure water, and left at 30° C. for 24 hours. Thereafter, 20 samples of the segment with a uniform angle from every region, were floated in the laboratory dishes, 6 cm across, containing 5 ml of the processing solution, and incubated again in the dark at 30° C. for 48 hours. The angle of the segments was measured and the average for the 20 samples was calculated.

| Compound | ppm | Degree of Inclination |
|---|---|---|
| 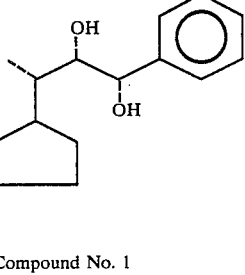 Compound No. 1 | 0.001<br>0.01<br>0.01<br>1 | 51.97 ± 10.5°<br>83.57 ± 10.5°<br>115.56 ± 10.5°<br>127.83 ± 10.5° |
| 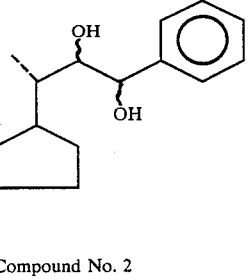 Compound No. 2 | 0.001<br>0.01<br>0.1<br>1 | 47.60 ± 10.5°<br>49.66 ± 10.5°<br>92.72 ± 10.5°<br>126.83 ± 10.5° |

TEST EXAMPLE 2

Effect of Brassinolide compounds on the growth promotion of sweet corn due to seed dipping treatment A given amount of sweet corn (variety: Honey bantam 20) were dipped into the diluted solution of test compounds which were adjusted to each concentration for 3 hours under the condition of 25° C.

After that, 6 treated seeds were washed in water, sown into the pot which packed a given amount of vermiculite and cultivated for 25 days in the climate chamber which was set the temperature of 15° C. to 20° C.

Plant height and weight of sweet corn were measured 25 days after seeding. Replication in this trial was carried out 3 times.

| | Test results | | |
|---|---|---|---|
| Test Compound | Concentration ppm | Plant height % | Plant weight % |
| Compound No. 1 | 1 | 114 | 126 |
| Compound No. 2 | 1 | 114 | 125 |
| Compound No. 5 | 1 | 111 | 119 |
| Compound No. 7 | 1 | 115 | 127 |
| Compound No. 8 | 1 | 114 | 126 |
| Compound No. 12 | 1 | 116 | 121 |
| Compound No. 16 | 1 | 115 | 121 |
| Brassinolide | 1 | 93 | 111 |
| Control | — | 100 | 100 |

TEST EXAMPLE 3

Effect of Brassinolide compounds on the growth of sweet corn due to seed dipping treatment under the condition of low temperature.

A given amount of sweet corn seeds (variety: Hanny bantam) were dipped into the diluted solution of test compounds which were adjusted to 0.1 and 1 ppm for 3 hours under the condition of 20° C.

After that, 4 treated seeds were washed into water, sown into the pot which filled up vermiculite and cultivated till they were grown up 3-leaf stages in greenhouse. Their sweet corn was exposed the low temperature of 5° C. for 5 days.

After that, they were returned to the ordinary temperature of greenhouse again and cultivated for 8 days there. Plant weight measured 33 days after seeding.

| | Test results | |
|---|---|---|
| Test compound | Concentration ppm | Plant weight % |
| Compound No. 1 | 0.1 | 120 |
| | 1 | 116 |
| Compound No. 2 | 0.1 | 121 |
| | 1 | 115 |
| Compound No. 8 | 0.1 | 122 |
| | 1 | 118 |
| Compound No. 14 | 0.1 | 120 |
| | 1 | 116 |
| Compound No. 16 | 0.1 | 123 |
| | 1 | 118 |
| Brassinolide | 0.1 | 115 |
| | 1 | 111 |
| Control | — | 100 |

TEST EXAMPLE 4

Effect of Brassinolide compounds on the cell elongation of cucumber

Cucumber seedlings were cultivated in the boxes which packed vermiculite till a true leaf development.

2 seedlings of cucumber were planted into the pots which contained 100 ml diluted solution of test compound which were adjusted to 1 ppm and cultivated for 5 days in the climate chamber under the condition of 20° C. to 25° C.

Petioles of first true leaf of cucumber were cut from the bottom and 1 cm segments from their petioles were made. Their segments were immediately fixed in FAA solution (Formalin, Acetic acid, Alcohol) and enclosed by paraffin.

Segments for preparats were made from their materials by Microtome. Cell size of their segments was measured by Microscope.

| Test Compound | Test results Concentration (ppm) | Cell size of cucumber (mμ) |
|---|---|---|
| Compound No. 1 | 1 | 135.1 |
| Compound No. 8 | 1 | 136.2 |
| Compound No. 15 | 0.5 | 129.0 |
| Compound No. 21 | 1 | 131.5 |
| Gibberellin | 1 | 120.3 |
| IAA | 1 | 105.5 |
| Control | — | 110.4 |

What we claim is:

1. A steroidal compound represented by the formula:

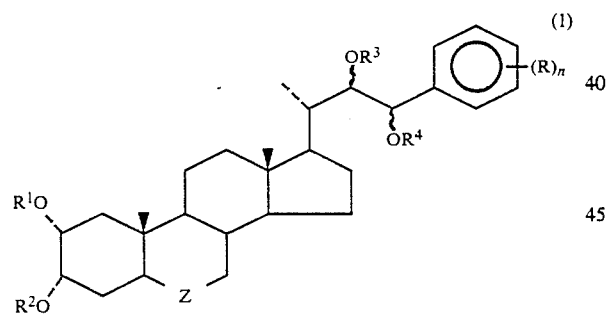

wherein
Z represents

n represents an integer of 1 to 3,
R represents hydrogen, halogen, CF$_3$, lower alkyl, lower alkoxy or —CO$_2$R', wherein R' represents hydrogen, alkali metal or lower alkyl, and
R$^1$, R$^2$, R$^3$ and R$^4$ represent hydrogen or acyl, respectively,
with the proviso that when n is 2 or 3, R may represent substituents which may be independent each from one or more of the others.

2. A steroidal compound according to claim 1, wherein Z represents

n represents an integer of 1 to 3, R represents hydrogen, halogen, CF$_3$, lower alkyl, or —CO$_2$R' wherein R' represents hydrogen, alkali metal or lower alkyl, and R$^1$, R$^2$, R$^3$ and R$^4$ represent hydrogen or acetyl, respectively, with the proviso that when n is 2 or 3, R may represent substituents which may be independent each from one or more of the others.

3. The steroidal compound according to claim 2 of the formula:

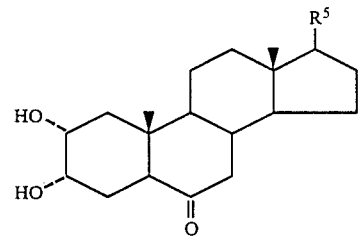

wherein R$^5$ is selected from the group consisting of

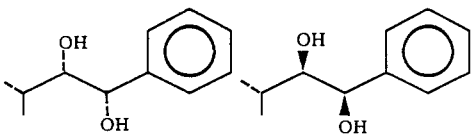

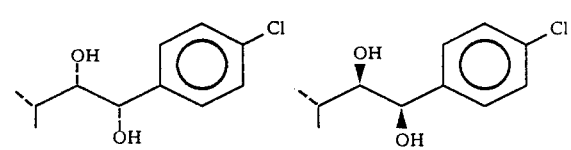

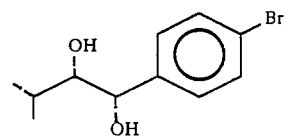

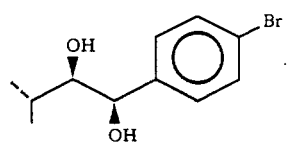

4. A plant growth regulating composition comprising an effective plant growth regulating amount of a steroidal compound of the formula:

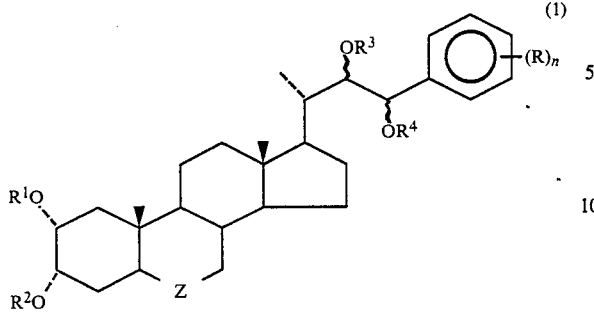

wherein
Z represents

n represents an integer of 1 to 3,
R represents hydrogen, halogen, CF$_3$, lower alkyl, lower alkoxy or —CO$_2$R', wherein R' represents hydrogen, alkali metal or lower alkyl, and
R$^1$, R$^2$, R$^3$ and R$^4$ represents hydrogen or acyl, respectively,
with the proviso that when n is 2 or 3, R may represent substituents which may be independent each from one or more of the others, and one or more acceptable adjuvants.

5. A method for regulating plant growth which comprises applying an effective plant growth regulating amount of a compound of the formula:

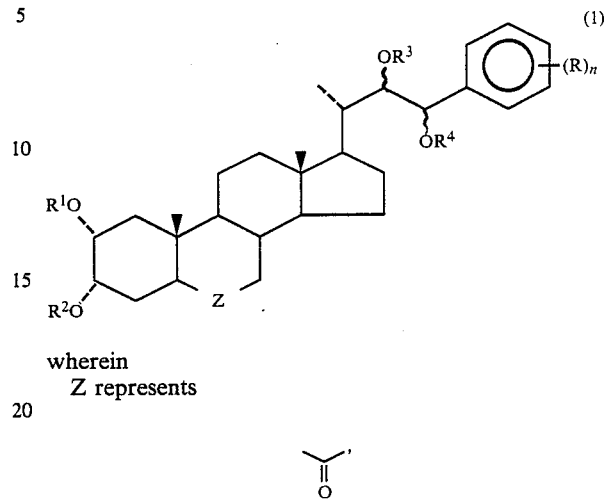

wherein
Z represents

n represents an integer of 1 to 3,
R represents hydrogen, halogen, CF$_3$, lower alkyl, lower alkoxy or —CO$_2$R', wherein R' represents hydrogen, alkali metal or lower alkyl, and
R$^1$, R$^2$, R$^3$ and R$^4$ represent hydrogen or acyl, respectively,
with the proviso that when n is 2 or 3, R may represent substituents which may be independent each from one or more of the others, to said plant and locus thereof.

* * * * *